(12) United States Patent
Ghaem et al.

(10) Patent No.: US 6,730,056 B1
(45) Date of Patent: May 4, 2004

(54) EYE IMPLANT FOR TREATING GLAUCOMA AND METHOD FOR MANUFACTURING SAME

(75) Inventors: Sanjar Ghaem, Chesapeake, VA (US); Iwona Turlik, Barrington, IL (US); Rudyard Istvan, Winnetka, IL (US)

(73) Assignee: Motorola, Inc., Schaumburg, IL (US)

( * ) Notice: Subject to any disclaimer, the term of this patent is extended or adjusted under 35 U.S.C. 154(b) by 250 days.

(21) Appl. No.: 09/668,054

(22) Filed: Sep. 21, 2000

(51) Int. Cl.[7] .......................... A61M 5/00; A61F 11/00
(52) U.S. Cl. ........................ 604/9; 604/8; 606/109
(58) Field of Search ..................... 604/8–10; 606/109

(56) References Cited

U.S. PATENT DOCUMENTS

| | | | | |
|---|---|---|---|---|
| 3,717,151 A | * | 2/1973 | Collett ..................... 604/106 |
| 3,788,327 A | * | 1/1974 | Donowitz et al. ........... 604/247 |
| 4,037,604 A | | 7/1977 | Newkirk .................... 128/50 |
| 4,043,346 A | * | 8/1977 | Mobley et al. .............. 604/107 |
| 4,140,126 A | * | 2/1979 | Choudhury ................ 606/194 |
| 4,175,563 A | | 11/1979 | Arenberg ................... 604/350 |
| 4,402,681 A | | 9/1983 | Haas et al. .................. 604/9 |
| 4,457,757 A | | 7/1984 | Molteno ..................... 604/294 |
| 4,521,210 A | | 6/1985 | Wong ......................... 604/8 |
| 4,692,142 A | | 9/1987 | Dignam et al. ............. 604/51 |
| 4,986,810 A | * | 1/1991 | Semrad ...................... 604/106 |
| 5,041,081 A | | 8/1991 | Odrich ....................... 604/9 |
| 5,073,163 A | | 12/1991 | Lippman ..................... 604/9 |
| 5,116,327 A | * | 5/1992 | Seder et al. ................. 604/284 |
| 5,127,901 A | | 7/1992 | Odrich ....................... 604/9 |
| 5,139,502 A | | 8/1992 | Berg et al. .................. 606/108 |
| 5,300,020 A | | 4/1994 | L'Esperance, Jr. ........... 604/9 |
| 5,433,701 A | | 7/1995 | Rubinstein .................. 604/8 |
| 5,454,796 A | | 10/1995 | Krupin ....................... 604/294 |
| 5,476,445 A | | 12/1995 | Baerveldt et al. ............ 604/8 |
| 5,558,629 A | | 9/1996 | Baerveldt et al. ............ 609/8 |
| 5,558,630 A | | 9/1996 | Fisher ......................... 609/8 |
| 5,702,414 A | | 12/1997 | Richter et al. ............... 606/166 |
| 5,868,697 A | | 2/1999 | Richter et al. ............... 604/8 |
| 5,968,058 A | | 10/1999 | Richter et al. | |
| 6,306,114 B1 | * | 10/2001 | Freeman et al. ............. 604/9 |
| 6,358,222 B1 | * | 3/2002 | Grundei ...................... 604/9 |

FOREIGN PATENT DOCUMENTS

WO WO9636377 11/1996

* cited by examiner

*Primary Examiner*—Angela D. Sykes
*Assistant Examiner*—Leslie R. Deak

(57) ABSTRACT

An eye implant for treating glaucoma includes a main conduit and a plurality of anchor members formed from a first resilient material. The anchor members are formed such that they are biased to a relaxed condition in a non-aligned position relative to the conduit. To facilitate insertion of the implant into the eye in a minimally invasive surgical procedure, the anchor members are secured together in an aligned condition relative to the conduit with a bonding material. A cutting surface or element is also applied to the anchor members to allow the implant to be inserted directly through the wall of the sclera. The cutting surface is formed of a second material different from the first material. The second material is adapted to dissolve or melt after the implant has been inserted into the eye. Similarly, the bonding material holding the anchor members together in an aligned condition can be made from a dissolveable or heat sensitive material to allow the anchor members to relax to their non-aligned position after insertion into the eye. In the non-aligned position, the anchor members secure the implant to the wall of the sclera. Alternatively, the bonding material holding the anchors together could be made from a material that is ablated away with a laser after the implant has been inserted into the eye.

28 Claims, 3 Drawing Sheets

EYE IMPLANT FOR TREATING GLAUCOMA AND METHOD FOR MANUFACTURING SAME

BACKGROUND OF THE INVENTION

A. Field of the Invention

This invention relates to the field of ophthalmic implants, and more particularly to a device for implantation in the eye for treatment of glaucoma.

B. Statement of Related Art

Glaucoma is an eye condition in which intraocular pressure is increased to an abnormal level. The increase in intraocular pressure causes an optical neuropathy to develop, namely death of certain cells in the retina, leading to restriction in the field of view and eventual blindness if left untreated.

A normal eye maintains proper intraocular pressure by means of circulation, within the eye, of a watery fluid known as aqueous humor. Aqueous humor is continuously produced by the ciliary body and passes through the pupil into the anterior chamber of the eye. In a healthy eye, the aqueous humor passes out of the eye through the trabeculum and the Canal of Schlemm. In persons suffering from glaucoma, the aqueous humor excretory pathway becomes blocked, whereby the aqueous humor cannot pass out of the anterior chamber of the eye at an adequate rate. This causes a rise in intraocular pressure, causing the damage to the retina and eventual blindness.

Glaucoma can be controlled in some patients via medications that increase the drainage of the aqueous humor. Where medication is unsuccessful, surgical treatment to provide a pathway for exit of aqueous humor is usually performed. Various surgical procedures have been developed to treat glaucoma and are described in the medical literature. Known surgical treatments have various shortcomings, including possible excessive loss of aqueous humor during the early post-operative period, and blockage of the passageway created during surgery by scarring.

Attempts have been made to improve surgical methods for treating glaucoma, including using opthalmic implants. These implants typically incorporate a drainage tube to provide a pathway for aqueous humor to exit from the anterior chamber of the eye, and various means to secure the implant to the wall of the sclera or surrounding tissue. A number of implants have been proposed in the patent literature. Representative patents include Richter et al., U.S. Pat. No. 5,968,058, Fisher, U.S. Pat. No. 5,558,630, Krupin, U.S. Pat. No. 5,454,796, Haas et al., U.S. Pat. No. 4,402,681, the patents to Baerveldt et al., U.S. Pat. Nos. 5,476,445 and 5,558,629; Molteno, U.S. Pat. No. 4,457,757; L'Esperance, Jr., U.S. Pat. No. 5,300,020, Lippmann, U.S. Pat. No. 5,073,163; Donowitz, et al., U.S. Pat. No. 3,788,327, and Wong, U.S. Pat. No. 4,521,210. The above-listed patents are fully incorporated by reference herein.

Many of the implants proposed in the above patents require relatively invasive surgical procedures to install the implant. See e.g. the Baerveldt and Wong patents. A group of physicians led by Dr. Reay Brown have proposed a T-shaped implant composed of tubing that is used to relieve intraocular pressure, but their method of implanting the device requires rather elaborate and invasive surgical procedures. Richter et al. proposes an implant that is inserted directly through the sclera in a rather less invasive procedure. Similarly, Donowitz et al. describes insertion of the implant through the cornea either directly, or through a prepared tract.

SUMMARY OF THE INVENTION

In a first aspect, an eye implant for treating glaucoma is provided. The implant includes a tubular body member, preferably made from a resilient elastomeric material, which forms a conduit having a first end and a second end. Aqueous humor flows through the conduit out of the eye. The conduit defines a longitudinal axis. A plurality of anchor members are integrally formed with the tubular body member. The anchor members, which can take the form of hollow tubes, are pre-stressed or otherwise formed in a manner or made from a suitable shape memory material such that they are biased to have a relaxed position in which they are oriented in a non-aligned position relative to the tubular body member, such as forming a T shape.

Prior to installation of the implant, a bonding material is applied to the anchor members to provide a means for retaining the anchor members together in an aligned condition relative to the tubular body member to facilitate insertion of the anchors through the wall of the sclera. The bonding material is made from a material that either melts or dissolves when the implant is inserted into the eye. Alternatively, the bonding material could be ablated by a laser after installation of the implant. In either case, the anchor members are released from their aligned condition and allowed to relax and orient themselves in their non-aligned position relative to the tubular body member, to thereby secure the implant against the wall of the sclera.

To further promote installation of the implant in a minimally-invasive surgical procedure, a cutting or blade element is formed on at least one of the anchor members, and preferably on all of them, either directly or by molding or bonding the cutting surface to the anchor members. The cutting element promotes ease of insertion of the anchor members (joined together by the bonding material) though the wall of the sclera. The cutting element is also formed of a dissolvable or meltable material, such that the cutting element also melts or dissolves after the implant has been installed in said eye.

In a preferred embodiment, the tubular conduit further includes a pressure-controlled valve. The valve is preferably adjustable after installation of the implant to change the flow characeristics of the conduit. In the illustrated embodiment, the valve comprises a section of the tubular body member, the section connected to the tubular body member by a flexible connecting portion. The section moves relative to the longitudinal axis in response to pressure changes in the conduit to thereby control the flow of aqueous humor through the conduit. The surgeon may ablate the flexible connecting portion with a laser to promote more flow of aqueous humor if greater pressure release is indicated postoperatively.

In another aspect of the invention, a method for manufacturing an eye implant for treating glaucoma is provided. The method comprises the steps of forming a conduit and a plurality of anchor members from a first resilient material, the anchor members formed such that they have a relaxed condition in a non-aligned position relative to the conduit, securing the anchor members together in an aligned condition relative to the conduit with a bonding material, and applying a cutting element to the anchor members. The cutting element is formed of a second material different from the first material, wherein the second material is adapted to dissolve or melt after the implant has been inserted into the eye.

The present inventive implant and method is believed to have a number of advantages over many prior art implants.

DETAILED DESCRIPTION OF THE PREFERRED EMBODIMENT

Figure 2:
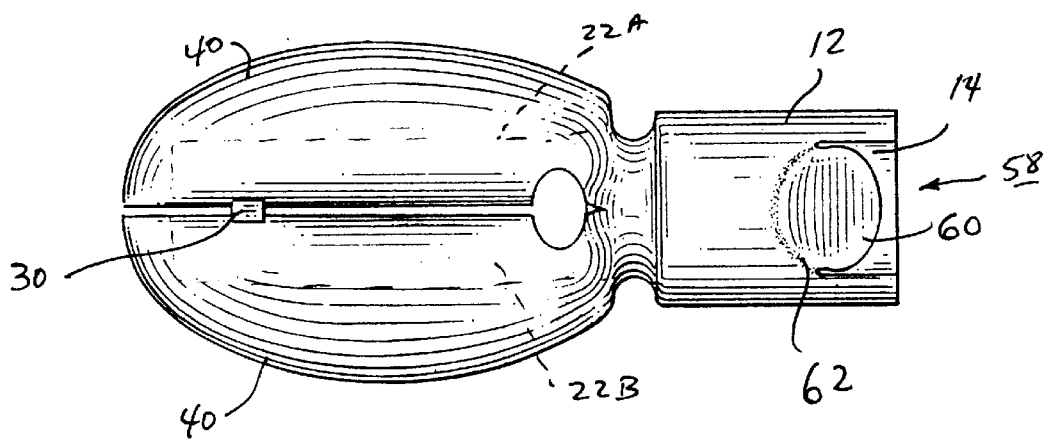
FIG. 2 is a plan view of the implant of FIG. 1.
Figure 3:
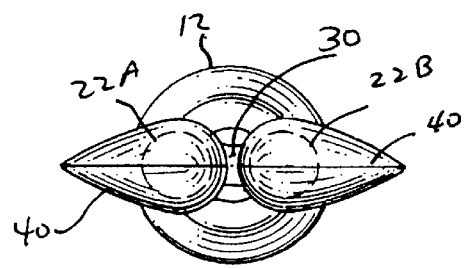
FIG. 3 is an end view of the implant of FIG. 1.
Figure 4:
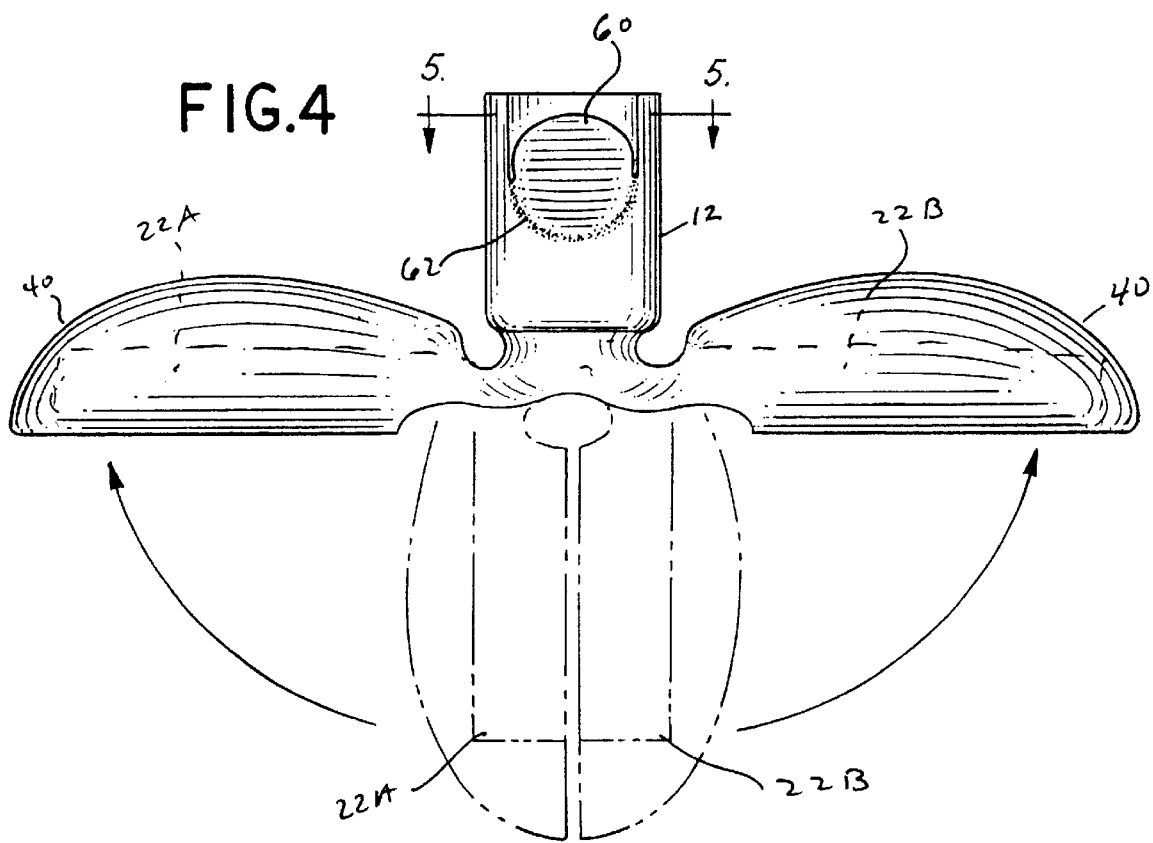
FIG. 4 is a plan view of the implant showing the relaxation of the anchor members to a non-aligned condition relative to the tubular body member, which would occur after the implant has been installed in the eye.
Figure 6:
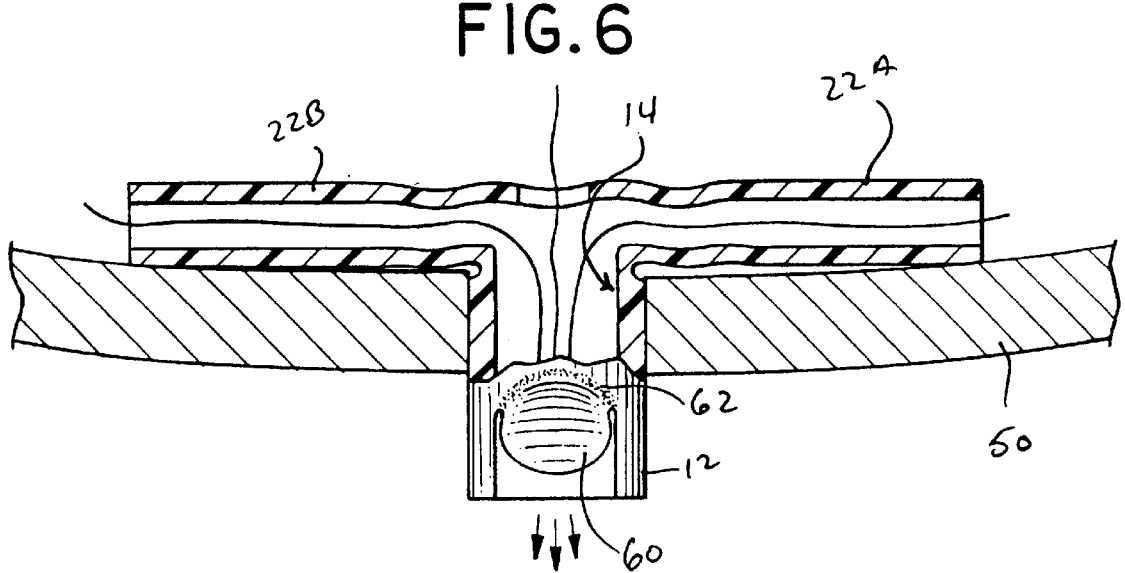
FIG. 6 is a cross-sectional view of a portion of the eye showing the implant in place.

Referring now to the FIGS. 1–4, an eye implant 10 for treating glaucoma is shown in several views. The implant 10 includes a tubular body member 12 forming a conduit 14 having a first end 16 and a second end 18. The conduit 14 provides a means for aqueous humor to flow out of the eye when the implant has been installed in the eye as shown in FIG. 6 and described subsequently. The conduit 14 and tubular body member 12 form a longitudinal axis 20 for the implant 10. The implant 10 is preferably made of a biocompatible, compliant, sterilizable, elastomeric material having shape memory properties described in further detail herein. Alternatively, the implant 10 is made from an engineered self-forming polymer which assumes a relaxed configuration in the form of a T as shown in FIG. 4.

Figure 1:
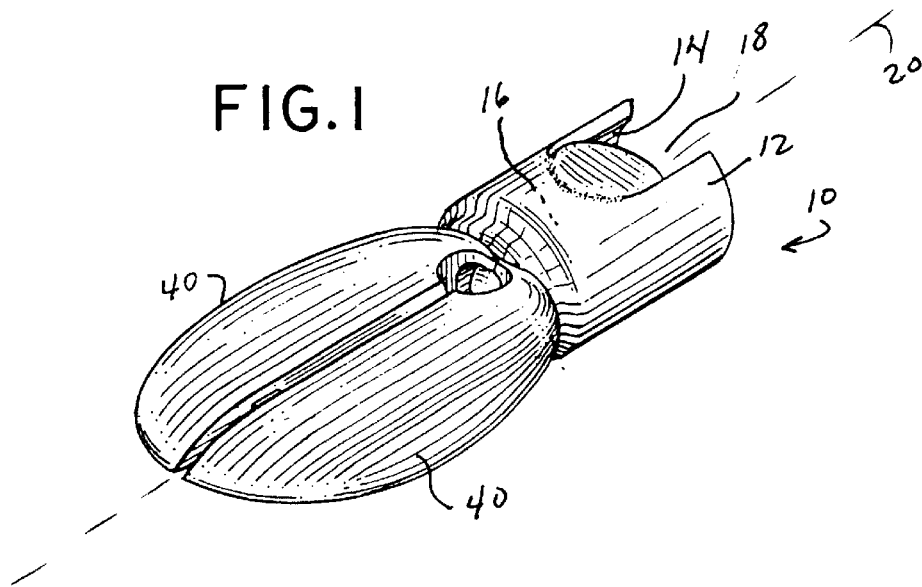
FIG. 1 is a perspective view of a preferred embodiment of the invention.

FIGS. 1–3 show the implant prior to installation in the eye. As noted above, the implant further includes a plurality of anchor members 22, which in the illustrated embodiment comprise two tubular anchors 22A and 22B. The anchor members 22A and 22B are integrally formed with the tubular body member 12. The anchors members 22A and 22B are pre-stressed, formed of a shape memory material, or otherwise constructed (e.g., from a self-forming polymer) such that they are biased towards a relaxed position in which they are oriented in a non-aligned condition relative to the tubular body member 12, as indicated in FIG. 4. The non-aligned condition could be in the form of a T or a Y or in some other shape. For example, if there are more than two anchor members 22 they would all be in a relaxed non-aligned condition relative to the tubular body member 12.

A means is provided for temporarily retaining the anchor members 22 together in an aligned relationship with the conduit 12, arranged parallel to the longitudinal axis, to thereby facilitate insertion of the implant through the wall of the sclera. In the illustrated embodiment, the retaining means comprises a bonding material 30 which is applied to the anchor members which bonds, i.e., secures, the anchor members together. After the implant has been installed in the eye, the bonding material 30 either dissolves, melts or is obliterated by means of a laser. Upon the release of the anchor members from the bonding material, the anchor members 22A and 22B are allowed to relax and orient themselves in the non-aligned condition relative to the tubular body member, as indicated by the arrows in FIG. 4. Other chemical or mechanical methods or structures for maintaining the anchor members in the aligned condition are considered equivalent to the use of a bonding material 30. A mechanical elastomeric material or structure could be ablated by means of a laser to release the anchors and allow them to reach their relaxed, non-aligned state.

Further, to promote direct insertion of the implant through the walls of the sclera without surgically constructing a passageway for the implant, cutting edges or surfaces 40 are formed or bonded to at least one of the anchor members, and preferably to all of the anchor members. The cutting edges 40 are formed of a dissolvable or meltable material, such that they facilitate insertion of the implant into the eye initially, but later gradually dissolve or melt after the implant has been installed in the eye.

In the illustrated embodiment, the anchor members 22A and 2B are tubular conduits, a shown in FIGS. 1 and 3. After they are relased from the bonding material, the anchor members 22A and 22B form a T shape, as shown in FIG. 4 and serve to abut against the interior surface of the sclera 50 as shown in FIG. 6 to thereby prevent the implant from being withdrawn from the eye. The tubular conduits in the anchor members 22A and 22B also form a passageway by which the aqueous humor may pass to the first end of tubular conduit and out the conduit, as indicated by the arrows in FIG. 6.

Alternative constructions for the anchors are of course possible. For example, the anchor members could be solid members. A greater number of anchors could also be provided, e.g. four or six of such anchors.

Figure 5:
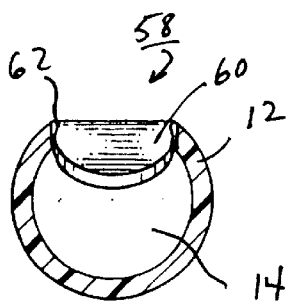
FIG. 5 is an end view of the tubular body member in an embodiment in which a pressure-controlled valve is formed in the upper surface of the body member.
Figure 7:
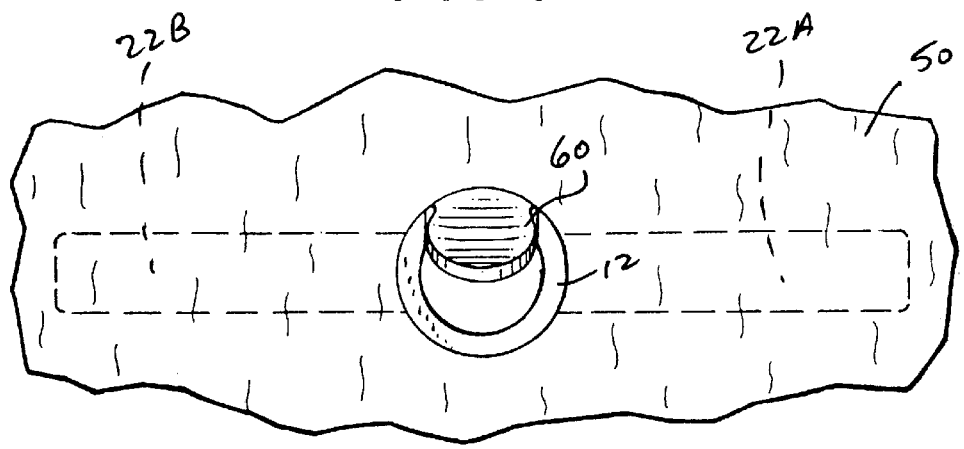
FIG. 7 is another view of the implant of FIG. 6 installed in the eye.

In a preferred embodiment, the implant includes a pressure-controlled valve formed in the tubular conduit 12. A variety of valves are suitable and are described in the patent literature. The presently preferred embodiment is where the valve formed in the surface of the tubular body member 12. As best shown in FIGS. 5, 6 and 7, the valve 58 comprises a section 60 of the tubular body member which is connected to the rest of the tubular body member by means of a flexible connecting portion 62. The section 60 is operative to move relative to the longitudinal axis of the implant in response to pressure changes in the conduit to thereby control the flow of fluid through the conduit. The flexible connecting portion 62 can be ablated by a laser after the implant has been installed in the eye to increase the flexiblity of the connecting portion, to thereby allow the section 60 to more readily move to a retracted position to allow greater flow rates of aqueous humor though the conduit. Such modifications could be done at any time post-installation of the implant.

Dissolving materials suitable for use for the bonding material joining the anchor members together, and for the cutting edges include Poly Vinyl Alcohol, Poly Vinyl Pyrolidone, enzymatic activated collagen, or other biomedically suitable materials. The implant may be chilled (e.g., to a temperature below 0 degrees C.) prior to use so as to increase the hardness and cutting ability of the cutting surfaces 40. Other suitable materials and methods may be selected by persons skilled in the art.

The implant can be installed in the anterior chamber of eye in a location and in a manner similar to those used by known implants, within the discretion of the surgeon. The patents to Richter et al., Baerveldt et al., Fisher, Kupin, and Lippmann describe various locations where the implant could be installed. One significant advantage of the present implant is that it does not require expensive, time consuming and invasive surgical procedures to implant the device, as it is designed to be inserted through the sclera in a minimally invasive procedure, without advance formation of passage or conduit to receive the implant. The device may be implanted with the aid of an eye implant tool. Such tools are known in the art. See, e.g., the patent to Richter et al.

From the foregoing, it will be appreciated that we have described a method for manufacturing an eye implant for treating glaucoma, comprising the steps of:

(1) forming a conduit 12 and a plurality of anchor members 22 from a first resilient material, said anchor members formed such that they have a relaxed position in a non-aligned condition relative to the conduit, as shown in FIGS. 4 and 6;

(2) securing the anchor members 22 together in an aligned condition relative to said conduit 12 with a bonding material 30; and (3) forming a cutting element 40 on the anchor members, the cutting element formed of a second material different from the first material. The cutting element 40 could be applied to the anchor members by any suitable technique, including the use of adhesives. The second material forming the cutting element is selected to either melt when exposed to temperatures of approximately 37 degrees C., or dissolved when placed in contact with a watery fluid such as the aqueous humor.

The preferred embodiment having been described with particularity, it will be appreciated that variation from the illustrated embodiment may be made without departure from the true spirit and scope of the invention. For example, the anchor members could be made from a self-cleaning material such as Teflon. The relaxed position the anchor members assume is not critical, nor is the number of such anchor members. This true spirit and scope is to be determined by reference to the appended claims.

We claim:

1. An eye implant for treating glaucoma, comprising:
    a tubular body member forming a conduit having a first end and a second end, said tubular body member defining a longitudinal axis;
    a plurality of anchor members, said anchor members integrally formed with said conduit and having a relaxed position in which said anchor members are oriented in a non-aligned condition relative to said tubular body member;
    a retaining material coupling the anchor members to the tubular member in an aligned condition; wherein the retaining material is dissolved or melted while the implant is positioned in the eye to allow the anchor members to move from the aligned condition to the non-aligned condition; and
    a cutting edge formed on at least one of said anchor members.

2. The implant of claim 1, wherein said plurality of anchor members comprises two anchors, said anchors and conduit forming a T after said retaining material releases said anchor members.

3. The implant of claim 1, wherein said anchors comprise hallow tubes.

4. The implant of claim 1, wherein said retaining material is made, in whole or in part, from a material selected from the group consisting of Poly Vinyl Alcohol, Poly Vinyl Pyrolidone, and enzymatic activated collagen.

5. The implant of claim 1, wherein said retaining material comprises a material dissolvable by laser obliteration while the implant is positioned in the eye.

6. The implant of claim 1, wherein said tubular conduit further comprises a pressure-controlled valve.

7. The implant of claim 6, wherein said pressure controlled valve comprises a section of said tubular body member, said section connected to said tubular body member by a flexible connecting portion, said section operative to move relative to said axis in response to pressure in said conduit to thereby control the flow of fluid through said conduit.

8. The implant of claim 1, wherein said tubular body member and plurality of anchors are made from a self-forming polymeric material.

9. The implant of claim 1, further comprising a cutting edge formed on at least one of said anchor members, the cutting edge facilitating insertion of said implant into said eye and wherein the cutting edge is formed of material that dissolves or melts while inserted in the eye.

10. The implant of claim 9, wherein the cutting edge comprises a material selected from the group consisting of Poly Vinyl Alcohol, Poly Vinyl Pyrolidone, and enzymatic activated collagen.

11. An eye implant for treating glaucoma, comprising:
    a tubular body member forming a conduit having a first end and a second end, said tubular body member defining an axis;
    a first and second anchor members, said first and second anchor members integrally formed with said conduit and having a first end and a second end, said first end connected to said tubular body member, said first and second anchor members pre-stressed such that said anchor members, in a relaxed condition, are oriented in a non-aligned position relative to said tubular body member;
    a bonding material connecting said first and second anchor members together in an aligned relationship with said conduit to facilitate insertion of said implant, wherein said anchor members are released from said bonding material to allow said anchor members to relax and orient themselves in said non-aligned position relative to said tubular body member after said implant has been installed in an eye; and
    a cutting element formed on said first and second anchor members, said cutting element formed of a dissolvable of meltable material, said cutting element facilitating insertion of said implant into said eye and dissolving or melting after said implant has been installed in said eye.

12. The implant of claim 11, wherein said first and second anchors comprise hollow tubes.

13. The implant of claim 11, wherein said first and second anchors comprise material which melts or dissolves when said implant is placed within said eye.

14. The implant of claim 11, wherein said bonding material comprises a material dissolvable by laser obliteration while the implant is positioned in the eye.

15. The implant of claim 11, wherein said tubular conduit further comprises a pressure-controlled valve.

16. The implant of claim 15, wherein said pressure controlled valve comprises a section of said tubular body member, said section connected to said tubular body member by a flexible connecting portion, said section operative to move relative to said axis in response to pressure in said conduit to thereby control the flow of fluid through said conduit.

17. The implant of claim 11, wherein said tubular body member and first and second anchors are made from a self-forming polymeric material.

18. The implant of claim 11, wherein the cutting element or the bonding material comprises a material selected from the group consisting of Poly Vinyl Alcohol, Poly Vinyl Pyrolidone, and enzymatic activated collagen.

19. The implant of claim 1 or claim 11, wherein said anchor members are made from Teflon.

20. The implant of claim 1 or claim 11, wherein said anchor members have an axial length greater than the axial length of said tubular body member.

21. An eye implant for treating glaucoma, comprising:
   a tubular body member forming a conduit having a first end and a second end, said tubular body member defining a longitudinal axis;
   a plurality of anchor members, said anchor members comprising hollow tubes integrally formed with said conduit and having a relaxed position in which said anchor members are oriented in a non-aligned condition relative to said tubular body member; and
   means for retaining the anchor members in a non-aligned condition for placement into the eye and for allowing the anchor members to move to a non-aligned condition while in the eye.

22. The implant of claim 21, further comprising a valve in said tubular body member.

23. The implant of claim 21, further comprising a cutting edge formed on said anchor members made from a material designed to melt or dissolve after said implant has been installed in said eye.

24. The implant of claim 23, wherein the cutting element comprises a material selected from the group consisting of Poly Vinyl Alcohol, Poly Vinyl Pyrolidone, and enzymatic activated collagen.

25. The implant of claim 21, wherein said tubular body member and anchor members are molded into a single piece of compliant, biocompatible material.

26. The implant of claim 21, wherein said plurality of anchor members comprises two anchors, said anchors and conduit forming a T after said retaining means releases said anchor members.

27. The implant of claim 21, wherein said plurality of anchor members comprise at least three anchors.

28. The implant of claim 21, wherein said tubular body member and said plurality of anchors are made from a self-forming polymeric material.

* * * * *